United States Patent [19]

Trampota et al.

[11] Patent Number: 5,162,499
[45] Date of Patent: Nov. 10, 1992

[54] SYNTHETIC PEPTIDES FOR THE TREATMENT OF AIDS

[75] Inventors: Miroslav Trampota, West Orange, N.J.; Matthew Pincus, Brooklyn, N.Y.

[73] Assignee: Heterocyclic Research, Inc., Milton, Fla.

[21] Appl. No.: 794,800

[22] Filed: Nov. 19, 1991

Related U.S. Application Data

[63] Continuation-in-part of Ser. No. 602,386, Oct. 22, 1990, abandoned, which is a continuation of Ser. No. 281,914, Dec. 7, 1988, abandoned, which is a continuation of Ser. No. 53,314, May 22, 1987, abandoned.

[51] Int. Cl.$^5$ .................. C07K 7/06; A61K 37/02
[52] U.S. Cl. ...................................... 530/328; 514/16
[58] Field of Search ........................... 530/328; 514/16

[56] References Cited

U.S. PATENT DOCUMENTS 4,737,487 4/1988 Watts et al. .................. 530/328

OTHER PUBLICATIONS

Cantor and Schimmel, Biophysical Chemistry, Part I: The Conformation of Biological Macromolecules, W. H. Freeman and Company, pp. 42–43, 72, 110–111 and 258 (1980).

Pharmaprojects, vol. 11, Tarr (Ed.), PJB Publications Ltd pp. 1–4 (May 1990).
Rudinger, Peptide Hormone, Parsons (Ed.), U Park Press, Baltimore, 1976.
Cram et al., Organic Chemistry, 2nd ed. McGraw-Hill Book Company, New York, pp. 607–613 (1964).
C. B. Pert et al., Proc. Natl. Acad. Sci., vol. 83, pp. 9254–9258, Dec. 1986.
M. R. Ruff et al., FEBS Letters, vol. 211, No. 1, pp. 17–22, Jan. 1987.
M. R. Pincus et al., Biochem. Biophys. Res. Comm., vol. 143, No. 1, pp. 248–251, 1987.
Anthony S. Fauci, Proc. Natl. Acad. Sci., U.S.A., vol. 83, pp. 9278–9283, Dec. 1986.

*Primary Examiner*—Y. Christina Chan
*Attorney, Agent, or Firm*—David J. Meyer

[57] ABSTRACT

Synthetic linear or cyclic peptides having the formula $[A]_x$-$[B]_x$-Ser-Ser-Ser-Asn-Tyr-$[C]_x$ wherein
A is L-Ala, DL-Ala, D-Ala, Gly, or Val;
B is L-Ala, DL-Ala, D-Ala, Gly, or Val;
C is L-Met, L-Met (O), Cys, Thr or Gly; and
x is an integer of from 0–1.

A method of treating AIDS by administering the synthetic peptides is also provided.

1 Claim, No Drawings

SYNTHETIC PEPTIDES FOR THE TREATMENT OF AIDS

CONTINUATION DATA

This application is a continuation-in-part of Ser. No. 602,386, now abandoned, filed Oct. 22, 1990, which was a file wrapper continuation of Ser. No. 281,914, filed Dec. 7,1988, now abandoned, which was a file wrapper continuation of Ser. No. 053,314, filed May 22, 1987, now abandoned.

TECHNICAL FIELD

This invention relates to synthetic peptides, and more particularly to pentapeptides, hexapeptides, heptapeptides and octapeptides which are useful for treating acquired immune deficiency syndrome and its related diseased (collectively AIDS). The present invention is also directed to a method of treating AIDS.

BACKGROUND OF THE INVENTION

Acquired immune deficiency syndrome and its related diseases was first recognized in about 1971, but it was only recently that the etiologic cause of the disease was isolated and identified as a human retrovirus named human immunodeficiency virus (HIV). HIV includes human T-lymphotropic virus type III (HTLV-III), lymphadenopathy-associated virus (LAV), and AIDS-associated retrovirus (ARV).

AIDS is generally recognized as epidemic in several areas of the world, including the United States. At present, the groups at highest risk of infection with HIV include homosexual and bisexual men and abusers of injected drugs. It is also known, however, that AIDS is transmitted heterosexually.

HIV acts by crippling the body's immune system. Particularly, HIV selectively attacks T4 cells, a subpopulation of helper/inducer lymphocytes which constituted part of the immune system. Infection with HIV results in both a reduction in the number and a change in function of the targeted T4 lymphocytes with eventual collapse of the immune system. Thus, the disease manifests itself as severe immunosuppression typically resulting in devastating opportunistic infections and neoplasias.

Present methods of treating AIDS are limited and largely ineffective. There is no known cure for AIDS, and in fact, effective treatment of a retroviral infection in man is unprecedented. Known therapies are generally limited to regimens designed to treat the secondary infections and neoplasias associated with AIDS. At present, AIDS has been treated with immunomodulators, such as cimetidine and interleukin-2, indomethacin, an antiinflammatory and prostaglandin inhibitor, and azidithymidine (AZT). None of the known therapies has been totally effective.

Recently, the subregion of the HIV external glycoprotein molecule, gp120, responsible for binding to brain membrane and human T cells has been identified as an octapeptide referred to as peptide T (Ala-Ser-Thr-Thr-Thr-Asn-Tyr-Thr). It has also been reported that peptide T and certain analogs thereof block the binding of HIV to T4 cells. C. B. Pert et al, Proc. Natl. Acad. Sci., Vol. 83, pp. 9254–9258, December 1986. Further, a correlation between the binding of peptide T to the T4 (CD4) surface molecule and the ability of the peptide to promote monocyte migration has also been reported. M. R. Ruff et al., FEBS Letters, Vol. 211, Number 1, pp. 17–22, January 1987.

A homology has been reported between peptide T and segments of other proteins, in particular, ribonuclease (segment 19-26), vasoactive intestinal peptide and a pentapeptide isolated from HTLV-III and LAV. M. R. Pincus et al., Biochem. Biophys. Res. Comm., Vol. 143, No. 1, pp. 248-251, 1987.

The present invention provides novel synthetic penta, hexa, hepta and octapeptides useful for the treatment of AIDS and a method for treating AIDS by administering the peptides of the invention.

SUMMARY OF THE INVENTION

The present invention involves synthetic penta, hexa, hepta and octapeptides useful as antagonists for blocking the binding of HIV to the T4 receptor molecule on human T-lymphocyte cells. The peptides of the invention may be linear or cyclic.

The presently preferred embodiment of the synthetic peptides of this invention is a linear octapeptide of the formula:

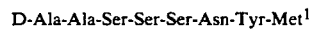

D-Ala-Ala-Ser-Ser-Ser-Asn-Tyr-Met[1]

[1] "D-ala" signifies the dextrorotary optical isomer of alanine. Except where specifically noted to the contrary, all amino acid residues are in the levorotary form.

The present invention also includes a method for treating AIDS by administering therapeutically effective doses of the peptides of the invention.

DETAILED DESCRIPTION OF THE INVENTION

Synthetic linear and cyclic penta, hexa, hepta and octapeptides are provided. The presently preferred peptide is a linear octapeptide having the amino acid sequence:

D-Ala-Ala-Ser-Ser-Ser-Asn-Tyr-Met.

wherein "D-Ala" refers to the dextrorotary optical isomer of alanine, and all other amino acid residues are in the levorotary form.

It should be understood that one or more of the amino acids in the peptides may be substituted N-alkyl amino acids instead of primary amino acids; methyl and ethyl substituents are preferred.

Further, the hydroxyl group (OH) side chains of one or more amino acids may be substituted with an ether or ester. Any substituted alkyl ester or ether may be used, for example, phenylethylester, benzylester, thiophene ethylester, phenylethylether, benzylether or thiophene ethylether. However, the presently preferred ethers are methyl, ethyl and propylethers, and the presently preferred esters are methyl, ethyl and propylesters.

The C terminal carboxyl group of the amino acid may be substituted with either an ester or an amide. Suitable esters include those previously mentioned. Suitable amides include formamide, N-methylamide and N-methylphenylamide.

The linear peptides of the present invention may be prepared by conventional solid or semisolid peptide synthetic techniques such as, for example, the methods described by B. Merrifield, Science, Vol. 232, pp. 341–347, 1986 and R. Schwyzer et al., Bioorganic Chemistry, Vol. 8, pp. 429–442, 1979, respectively. Classical stepwise or fragment condensation solution techniques may also be employed to synthesize the peptides of the invention. Solid phase synthesis is presently preferred.

The cyclic peptides of the invention may be prepared by known techniques, such as, for example, the method described by Y. Hamada, Tetrahedron Letters, Vol. 26, p. 5155, 1985.

Solid phase synthesis of the linear peptides of the invention comprises the steps of:

1. Binding a protected C-terminal amino acid to a polymeric support using an ester or amide linkage. Suitable polymers include aminomethyl resin, polyamide peptide resin, phenylacetamidomethyl resin (PAM), and benzhydrylamine resin. While any linking agent known to those skilled in the art may be used, it is presently preferred to use dicyclohexylcarbodiamide (DCC). The C-terminal amino acid may be protected with either t-butoxycarbonyl (BOC) or fluoronylmethoxycarbonyl (FMOC);

2. Coupling the C-terminal amino acid with a protected amino acid, preferably either a BOC protected symmetric anhydride amino acid or a FMOC protected pentafluorophenyl (PFP) active ester of an amino acid, at $-20°$ C.$-60°$ C. in a suitable solvent. Useful solvents include dimethylformamide (DMF), diethylformamide, ethylacetate, tetrahydrofuran and dichloromethane, preferably DMF. The symmetric anhydride amino acid may be obtained by converting a BOC protected amino acid in accordance with known techniques, such as, for example, the method described by B. Merrifield, Science, Vol. 232, pp. 341-347, 1986. Conversion of an FMOC protected amino acid to its PFP active ester may be carried out by conventional methods such as, for example, the method described by R. P. Andrews, Nature, Vol. 319, pp. 429-30, 1986;

3. Cleaving the amino protecting group to thereby obtain a free amino polymer supported dipeptide. Suitable cleaving agents include trifluoromethane sulfonic acid, trifluoroacetic acid, anhydrous hydrogen fluoride or by catalytic hydrogenolysis. Palladium or platinum, particularly supported on carbon, are suitable catalysts.

4. Repeating steps 2 and 3 until the desired length peptide is obtained.

Prior to beginning to synthesis, it may be also desirable to protect the chemically reactive side chains of serine, threonine and tyrosine. Suitable protecting groups are those which do not interfere with subsequent reactions and which can be removed under conditions which do not cause undesired reactions at other sites on the amino acids or products produced therefrom. For this purpose, the protecting groups described by T. W. Green in *Protective Groups in Organic Synthesis*, John Wiley & Son, 1981 are considered useful. The preferred protecting groups are benzyl or substituted benzyl wherein the substituent is, for example, alkyl or alkoxy having from one to four carbon atoms, or halo (Cl, Br, F, I). It should be understood that the exact chemical structure of the protecting group is not critical. The important consideration is that the protecting group can be readily removed, leaving the protected group unchanged. Accordingly, the selection and identification of an appropriate protecting group is considered within the purview of those skilled in the art.

During the solid phase synthesis the coupling reaction of step 2 may be carried out manually or semiautomatically in accordance with known techniques. Typically, coupling requires about 30 minutes to 6 hours, with rapid shaking or other suitable means of agitation. When coupling is completed, the resin is washed with appropriate solvents, such as DMF, tetrahydrofuran, and ethylacetate. Prior to each coupling, protecting group is removed by treating with the appropriate reagent for 30-90 minutes at $-5°$ C.$-+25°$ C. to obtain thereby a free amino group. The reagent used depends on the protective group to be removed. For example, for removing BOC, it is preferred to use trifluoroacetic acid in methylene chloride. FMOC is preferably removed with 20% piperidine in DMF.

Once the desired length peptide is obtained, the peptide is cleaved from the polymeric support by treating with anhydrous hydrogen fluoride, methanesulfonic acid/trifluoroacetic acid or other suitable reagents as are known to those skilled in the art. The peptide thus obtained is then typically purified by conventional methods such as lyophilization, crystallization, HPLC or other known purification techniques.

The structures of the synthesized peptides are readily confirmed by known methods such as elemental analysis, amino acid sequencing and nuclear magnetic resonance.

The activity of the peptides synthesized is generally evaluated by chemotaxis assay, such as described by Ruff, et al., FEBS, Vol. 211, Number 1, page 17-22, 1987. Briefly, monocyte migration is directly observed in a chemotaxis chamber. Additionally, quantitative binding of radiolabelled peptides of the invention to T4 receptors on T-lymphocytes is a useful tool for evaluating the activity of the peptides.

Semisolid phase synthesis of the peptides of the invention is virtually identical to the solid phase method, except that in the semisolid technique, substituted phenylazobenzenesulfoxidoalkyl ($C_1-C_6$) esters (PAZBS) provide a support for the C terminal amino acids.

EXAMPLE 1

Solid Phase Preparation of
BOC-D-Ala-L-Ala-Ser(OBz)-Ser(OBz)-Ser(OBz)-MET-PAM Resin 5 gm of PAM Methionine, t-BOC resin (0.67 mmol/gm) was shaken for 30 minutes with 25 ml of 50% methylene chloride-trifluoroacetic acid at 5° C. The resin obtained thereby was washed twice with 50 ml of methylene chloride and dried in vacuo to obtain H-MET-PAM resin (4.93 gm).

H-MET-PAM resin (3.50 gm) was coupled with a symmetric anhydride prepared from 10 mmol of BOC-YTR(OBz) and 5 mmol DCC in DMF at room temperature for 60 minutes with vigorous shaking. Upon completion of coupling (as determined by ninhydrin monitoring) the resin thus obtained was washed with 20 ml methylene chloride (with shaking) for 10 minutes, shaken with 10 ml 1:1 methylene chloride-trifluoroacetic acid (30 minutes), washed with N-ethyl morpholine (5% in methylene chloride for 5 minutes) and again washed with 25 ml methylene chloride for 5 minutes to obtain H-TYR(OBz)-MET-PAM resin (3.52 gm). The resin thus obtained was repeatedly coupled, deprotected and washed (steps 2 and 3). The coupling reagents used, in order of use were BOC-ASN-sym.anhydride(+3 equiv. HOBZ), BOC-SER(OB$_z$)-sym. anhydride-3 times, BOC-ALA-sym. anhydride and BOC-D-ALA-sym. anhydride. The yield of the final BOC-octapeptide-PAM resin was 99%. Intermediate penta, hexa, and hepta BOC-peptides were isolated in yields of 99.9%, 99.8%, and 99.9%, respectively.

EXAMPLE 2

Preparation of H-SER-SER-ASN-TYR-MET

BOC-SER-(OBz)-SER(PBz)-ASN-TYR(OBz)-MET-PAM resin (1.0 gm) was placed in a 150 ml one neck round bottom flask equipped with a stirring bar 2.0 gm ethane dithiol-thioanisole (1:2) was added to the contents of the flask and stirred at room temperature for 15 minutes. Then, 15 ml of a solution of trifluoromethane sulphonic acid in trifluoroacetic acid was added and the reaction mixture was stirred for 2 hours to obtain the penta peptide. The contents of the flask were filtered and the resulting peptide was precipitated with diethylether. The crude peptide thus obtained was dissolved in distilled water and then lyophylized. An 85% yield of pure pentapeptide was recovered.

On analysis the peptapeptide had the following characteristics:

M.W. 660.64.
Elemental Analysis: C24 H36 N6 O10 S.
MS:600.64

| | Amino acid analysis | | |
|---|---|---|---|
| | Nanomole | Theoretical | Actual |
| ASP | 2.68 | 1 | 1.02 |
| SER | 5.20 | 2 | 1.98 |
| TYR | 2.66 | 1 | 1.01 |

EXAMPLE 3

Preparation of Cyclo
(D-Ala-L-Ala-Ser-Ser-Ser-Asn-Tyr-Met)

83 mg (0.1 mmol) of linear D-Ala-Ala-Ser-Ser-Ser-Asn-Tyr-Met was suspended in 120 ml of DMF. Diphenyl phosphoazidate (0.125 mmol) was then added under rapid stirring. The reaction mixture was stirred for 6 days, then evaporated in vacuo, and pure cyclic octapeptide was isolated by HPLC. A yield of 28 mg (31%) of the cyclic peptide was recovered.

M.W. 582.62.
C24 H34 N6 O9 S.
MS 582.619

| T | C 49.47 | H 5.88 | N 14.42 |
|---|---|---|---|
| A | 49.04 | 6.32 | 14.12 |

EXAMPLES 4-8

A comparative study comparing the chemotactic activity of the peptides of the invention with the chemotactic activity of peptide T (C. B. Pert et al., Proc. Natl. Acad. Sci., Vol. 83, pp. 9254-9258, 1986) was undertaken. The results of the study, which are summarized in Table II, demonstrate that the peptides of the invention exhibit significant chemotactic activity at concentrations of $10^{-12}$M. The chemotaxis assay was performed generally in accordance with the technique described by Ruff et al., FEBS Letters, Vol. 211, No. 1, pp. 17-22, 1987. Human monocytes were obtained by the known technique of layering heparinized blood on FICOLL-HYPAQUE differential dentrifugation medium in a centrifuge tube and spinning to separate the red blood cells from plasma and the monolayered monocytes. The monocytes were pipetted off and then washed with physiological saline.

TABLE 1

Linear peptides having the following amino acid sequences were prepared by the solid and semisolid synthetic methods previously described.

| Peptide | M.W. | | Elemental Analysis % | | |
|---|---|---|---|---|---|
| | | | C | H | N |
| C27 H41 N7 O12 S SER—SER—SER—ASN—TYR—MET | 687.71 | T | 47.15 | 6.02 | 14.26 |
| | | A | 46.90 | 6.41 | 14.03 |
| C30 H46 N8 O13 S ALA—SER—SER—SER—ASN—TYR—MET | 758.78 | T | 47.49 | 6.11 | 14.77 |
| | | A | 47.12 | 6.50 | 14.32 |
| C33 H51 N9 O14 S D—ALA—ALA—SER—SER—SER—ASN—TYR—MET[2] | 829.86 | T | 47.76 | 6.19 | 15.19 |
| | | A | 47.33 | 6.61 | 15.04 |
| C22 H32 N6 O11 SER—SER—SER—ASN—TYR | 556.52 | T | 47.48 | 5.79 | 15.10 |
| | | A | 47.30 | 5.91 | 14.85 |
| C25 H37 N7 O12 ALA—SER—SER—SER—ASN—TYR | 627.59 | T | 47.85 | 5.94 | 15.62 |
| | | A | 47.68 | 6.32 | 16.94 |
| C28 H42 N8 O13 ALA—ALA—SER—SER—SER—ASN—TYR | 698.66 | T | 48.13 | 6.06 | 16.04 |
| | | A | 47.93 | 6.51 | 15.90 |
| C24 H35 N7 O12 SER—SER—SER—ASN—TYR—GLY | 613.58 | T | 46.98 | 5.75 | 15.98 |
| | | A | 46.66 | 6.08 | 15.71 |
| C30 H45 N9 O14 D—ALA—ALA—SER—SER—SER—ASN—TYR—GLY | 755.42 | T | 47.70 | 6.00 | 16.69 |
| | | A | 47.20 | 6.51 | 16.28 |

T = Theoretical Amounts; A = Actual Amounts

The agarose plates were also prepared in accordance with conventional methods. Agarose type II (0.4 g), available from Sigma Chemical, and LITEX gelatin (0.3 g) were combined and heated until the gelatin was thoroughly dissolved. RMPI-HANK buffer (4 ml), distilled water (15.2 ml) and saturated NaHCO3 solution (0.8 ml) were then added to the agarose gelatin and mixed to homogeneity. 5 ml aliquots of the resulting solution were poured into plastic petri dishes (FALCON 55 mm) and allowed to gel. After the agarose has sufficiently hardened, wells, 3 mm in diameter were cut in the agarose, such that each dish had six rows of wells radiating from the center of the dish, each row containing three wells spaced apart by a distance of 3 mm. Thus, each plate was used to assay two test samples in triplicate. 8 ul of the test peptide (in 120 mM HEPES buffer) was placed on the outermost well, 8 ul of monocyte cell solution was placed in the center well and 8 ul of RPMI-HANKS buffer was placed in the innermost well. The migration of monocytes was visually observed and the number of migrating cells was determined. A chemotactic index was calculated as the number of cells which migrated toward the attractant, i.e., test peptide or control, less the number of cells that migrated towards the buffer divided by 10. Formyl-Met-Leu-Phe (FMLP) and (D-Ala)Peptide-T were used as positive control and HEPES buffer and Leu-Gly-Gly were used as negative controls.

TABLE II

| | Attractant | Concentration | Chemotactic Index |
|---|---|---|---|
| Control | | | |
| 1 | Formyl—Met—Leu—Phe | $10^{-7}M$[1] | 2.8 |
| 2 | (D—Ala) Peptide T | $10^{-10}M$ | 2.0 |
| | | $10^{-11}M$ | 7.0 |
| | | $10^{-12}M$ | 0.5 |
| 3 | Hepes buffer (neg. contt.) 120 mM | | 0 |
| 4 | Leu—Gly—Gly (neg. cont.) | all conc.s | 0 |
| Example[2] | | | |
| 4 | Octapeptide (D—Ala) | $10^{-9}M$ | 4.8 |
| | | $10^{-10}M$ | 4.5 |
| | | $10^{-11}M$ | 5.3 |
| | | $10^{-12}M$ | 5.1 |
| 5 | Octapeptide (L—Ala) | $10^{-9}M$ | 3.5 |
| | | $10^{-10}M$ | 3.2 |
| | | $10^{-11}M$ | 3.8 |
| 6 | Heptapeptide | $10^{-9}M$ | 4.9 |
| | | $10^{-10}M$ | 4.7 |
| | | $10^{-11}M$ | 5.1 |
| 7 | Hexapeptide | $10^{-9}M$ | 4.6 |
| | | $10^{-10}M$ | 5.1 |
| | | $10^{-11}M$ | 5.3 |
| 8 | Pentapeptide | $10^{-9}M$ | 5.0 |
| | | $10^{-10}M$ | 4.8 |
| | | $10^{-11}M$ | 6.0 |

[1] Concentration of FMLP as reported by Ruff et al. FEBS Letts., vol. 211, pp. 17–22 (1987).
[2] All peptides tested were linear peptides.

The results summarized in Table II, demonstrate that the peptides of the invention are able to attract human monocytes. As previously discussed, it has been found that there is an excellent correlation between the ability of the peptide to promote monocyte migration and the binding of T peptide to T4 receptors. (See M. R. Ruff et al., FEBS Letters, Vol. 211, No. 1, pp. 17–22, 1987).

The results presented in Table II for Example 4 demonstrate that the preferred embodiment of the present invention is more effective than peptide T in the chemotaxis assay described by Ruff et al. (1987). The synthetic octapeptide tested in Example 4 [Table II] has the formula:

D-Ala-Ala-Ser-Ser-Ser-Asn-Tyr-Met wherein "D-Ala" indicates the dextrorotary optical isomer of alanine, and where all other amino acid residues are int the levorotary form.

According to a further preferred embodiment of the present invention, a method of treating AIDS with the synthetic peptides described herein is provided. In accordance therewith, a therapeutically effective dosage of the peptide, which may be obtained according to the methods described hereinabove, is administered to a patient infected with HIV. A therapeutically effective dosage may be from about 0.05 ∝ 10 mg of peptide administered parenterally once per day.

The dosage level may, of course, be adjusted to provide optimum therapeutic response. For example, several divided doses may be administered daily, or the dose may be proportionately reduced, as indicated by the exigencies of the therapeutic situation.

The peptide may suitably be administered orally or parenterally, generally, together with a pharmaceutically acceptable carrier. Pharmaceutical forms suitable for injectable use include sterile solutions, or dispersions and sterile powders for extemporaneous preparation of sterile solutions.

The carrier can be a solvent or a dispersing medium and such carriers and excipients as are known to those skilled in the art are useful.

The advantages of the therapeutic method of the present method are apparent. AIDS has already reached epidemic proportions in the United States. Because of the long incubation period from infection to the manifestation of the disease, the number of persons already infected with HIV is not known, but the number of persons with AIDS is expected to dramatically increase in the next few years. The present invention provides a treatment for AIDS, which unlike presently available therapies, is directed to blocking the attachment of HIV to the virus targeted human T-lymphocytes.

While preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, the scope of the invention being defined by the following claims.

What is claimed is:

1. A synthetic peptide consisting of the amino acid sequence:

D-Ala-Ala-Ser-Ser-Ser-Asn-Tyr-Met, wherein the N-terminal alanine residue is the dextrorotary optical isomer, and all other residues are in the levorotary form.

* * * * *